United States Patent [19]

Furutachi et al.

[11] Patent Number: 4,556,630
[45] Date of Patent: Dec. 3, 1985

[54] COLOR PHOTOGRAPHIC LIGHT-SENSITIVE MATERIAL

[75] Inventors: Nobuo Furutachi; Kotaro Nakamura; Takeshi Hirose, all of Kanagawa, Japan

[73] Assignee: Fuji Photo Film Co., Ltd., Kanagawa, Japan

[21] Appl. No.: 622,805

[22] Filed: Jun. 20, 1984

[30] Foreign Application Priority Data

Jun. 20, 1983 [JP] Japan ................. 58-110596

[51] Int. Cl.[4] .................. G03C 7/40; G03C 7/26
[52] U.S. Cl. ...................... 430/372; 430/387; 430/393; 430/505; 430/555; 430/558
[58] Field of Search ............ 430/372, 387, 393, 555, 430/558, 505

[56] References Cited

U.S. PATENT DOCUMENTS

| | | | |
|---|---|---|---|
| 4,351,897 | 9/1982 | Aoki et al. | 430/555 |
| 4,383,027 | 5/1983 | Ishikawa et al. | 430/372 |
| 4,385,111 | 5/1983 | Nakamura et al. | 430/558 |
| 4,413,054 | 11/1983 | Mitsui et al. | 430/387 |
| 4,463,085 | 7/1984 | Mitsui et al. | 430/555 |

*Primary Examiner*—J. Travis Brown

*Attorney, Agent, or Firm*—Sughrue, Mion, Zinn, Macpeak & Seas

[57] ABSTRACT

A silver halide color photographic light-sensitive material comprising a support having coated thereon at least one silver halide emulsion layer, the color photographic light-sensitive material having a photographic layer containing at least one magenta coupler represented by the following general formula (I) or (II):

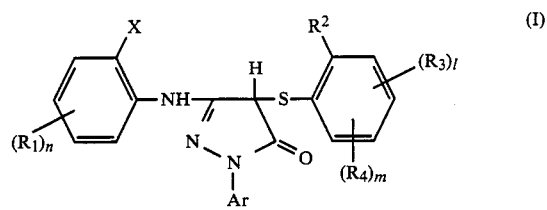

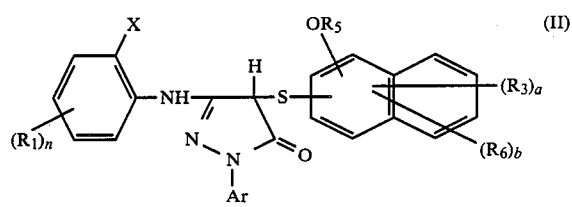

26 Claims, No Drawings

COLOR PHOTOGRAPHIC LIGHT-SENSITIVE MATERIAL

FIELD OF THE INVENTION

The present invention relates to a color photographic light-sensitive material, and more particularly to a color photographic light-sensitive material containing a novel 2-equivalent magenta coupler, which exhibits superior photographic properties despite variations in the pH of the color developing bath, reduced stain formation during development processing, and color images fast to heat and light.

BACKGROUND OF THE INVENTION

Various pyrazolone derivatives are known as magenta color image forming couplers (referred to hereinafter simply as "magenta couplers"). However, these pyrazolone derivatives generally have low color forming efficiency (ratio of conversion of the coupler into a dye) when contained in photographic light-sensitive materials. In particular, known four-equivalent couplers, in which the coupling position is not substituted, have a low color forming efficiency, resulting in the conversion of only about ½ mol of dye per mol of the coupler present.

To improve color forming efficiency, so-called two-equivalent magenta couplers are known, in which a substituent is present at the coupling active position of a pyrazolone type magenta coupler, and the substituent is removed in the color development step.

Among these two-equivalent magenta couplers, a large number of magenta couplers are provided in which a substituent is connected to the coupling active position, through a sulfur atom as described, for example, in U.S. Pat. Nos. 3,214,437, 3,227,554, 3,701,783 and 4,032,346, Japanese Patent Publication No. 34044/78, Japanese Patent Application (OPI) Nos. 62454/80 and 35858/82 [the term "OPI" as used herein refers to a "published unexamined Japanese patent application."], etc.

It has been found that when magenta couplers capable of releasing an arylthio group present at the coupling active position as described in U.S. Pat. Nos. 3,227,554 and 3,701,783 and Japanese Patent Publication No. 34044/78, are used in a color photographic light-sensitive material and color images are formed, the light fastness of the color images is inferior. On the other hand, the couplers which release an arylthio group as described in Japanese Patent Application (OPI) No. 35858/82 certainly provide color images having improved light fastness.

However, although they represent a certain improvement over four-equivalent magenta couplers, these two-equivalent magenta couplers retain the disadvantage that stains (increase in color density in unexposed areas) are formed during development processing.

The stains occurring in unexposed areas of silver halide color photographic light-sensitive materials are undesirable and determine whether whiteness of the non-image areas is good or bad. Further, the stains adversely affect the color turbidity of the images and the visual sharpness of the images. Particularly in the case of reflective photographic materials, such as photographic color papers, the reflective density of the stains may be theoretically more increased by several times than the transmission density thereof. Therefore, such stains are very important since even a slight degree of stain can adversely affect image quality.

The stains occurring in silver halide color photographic light-sensitive materials are generally classified into four groups depending on the cause of the stain. One stain is formed after the production of the photographic light-sensitive material and before the processing thereof by exposure to heat or humidity. A second stain is caused by development fog of the silver halide. A third stain results from color contamination due to the presence of color couplers in a development processing solution (for example, aerial fog, etc.) or results from the formation of a dye by the reaction with a coupler of an oxidized developing agent, e.g., a developing agent remaining in the silver halide emulsion layer which is oxidized by a bleach solution or oxygen in the air, etc. (for example, a bleaching stain, etc.). A fourth stain results from changes in developed photographic materials with the passage of time due to light, humidity or heat. The present invention relates to stains due to the development processing of photographic materials containing 2-equivalent magenta couplers, i.e., the present invention relates to the third and fourth types of stains described above.

It is unusual to prepare a new solution for the development processing before every development processing. In practice, developing solutions are reclaimed by adding a replenishing developing solution in an amount which depends on the amount of photographic materials developed. However, the composition of a developing solution cannot be maintained merely by adding components which are consumed by development.

In general, solutions for development processing include a color developing solution, a stopping solution, a bleaching solution, and a fixing solution or a bleach-fixing (blixing) solution. Since the processing temperature is typically maintained at a high temperature of from 31° C. to 43° C., the compositions of the processing solutions can be changed by several factors. For example, components such as the developing agent may decompose after a long period of time or oxidize when brought in contact with the air. It is also possible for the components contained in the photographic light-sensitive materials to be dissolved and to accumulate in the solution during the processing of the photographic light-sensitive materials. In addition, one processing solution may be carried over into the following bath by becoming attached to the photographic material, by which the processing solution becomes a "running" solution. To eliminate such problems, reclaimation procedures in which depleted chemicals are supplementarily added to the solution and/or undesirable components are removed are carried out, but these procedures are still insufficient.

Photographic light-sensitive materials containing 2-equivalent magenta couplers have a notable tendency to form stains in running solutions. Moreover, the occurrence of such stains cannot be sufficiently prevented by using known arylthio releasing type couplers.

As the result of the detailed investigations, it has now been found that a series of magenta couplers exhibit remarkably reduced occurrence of stains without adversely affecting the light fastness of color images.

SUMMARY OF THE INVENTION

Therefore, an object of the present invention is to provide a color photographic light-sensitive material which forms color images which are fast to light and in which the occurrence of stain is reduced when the photographic light-sensitive material is subjected to development processing.

Another object of the present invention is to provide a color photographic light-sensitive material with superior photographic properties despite variations in the pH of the color developing solution.

Still another object of the present invention is to provide a color photographic light-sensitive material containing a low cost two-equivalent magenta coupler by a simple production process.

A further object of the present inventiion is to provide a color photographic light-sensitive material having improved color forming efficiency, reduced, coupler content, and reduced silver halide content.

A still further object of the present invention is to provide a color photographic light-sensitive material which does not have an influence on silver halide after color development processing.

Other objects of the present invention will become apparent from the following detailed description and examples.

The above-described objects of the present invention can be attained by a silver halide color photographic light-sensitive material comprising a support having coated thereon at least one silver halide emulsion layer, the color photographic light-sensitive material having a photographic layer containing at least one magenta coupler represented by the following general formula (I) or (II):

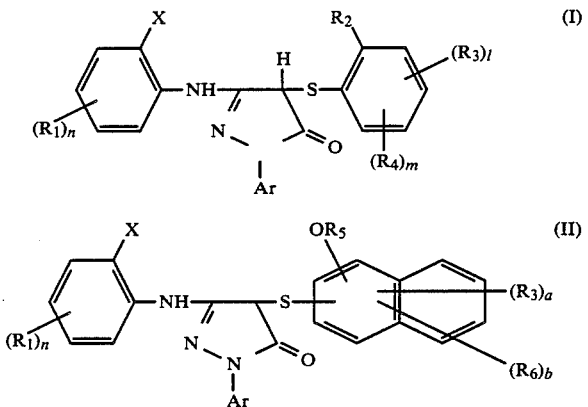

wherein Ar represents a phenyl group substituted with at least one of a halogen atom, an alkyl group, an alkoxy group, an alkoxycarbonyl group or a cyano group; X represents a halogen atom or an alkoxy group; $R_1$ represents hydrogen, a halogen atom, an alkyl group, an alkoxy group, an acylamino group, a sulfonamido group, a sulfamoyl group, a carbamoyl group, a sulfadiacylamino group, an alkoxycarbonyl group, an alkoxysulfonyl group, an aryloxysulfonyl group, an alkanesulfonyl group, an arylsulfonyl group, an alkylthio group, an arylthio group, an alkyloxycarbonylamino group, a ureido group, an acyl group, a nitro group or a carboxy group; $R_2$ represents a halogen atom, a hydroxy group, an amino group, an alkyl group, an alkoxy group or an aryl group; $R_3$ represents an amino group, an acylamino group, a ureido group, an alkoxycarbonylamino group, an imido group, a sulfonamido group, a sulfamoylamino group, a nitro group, an alkoxycarbonyl group, a carbamoyl group, an acyl group, a cyano group or an alkylthio group; $R_4$ represents hydrogen, a halogen atom, a hydroxy group, an alkyl group, an alkoxy group or an aryl group; at least one of $R_2$ and $R_4$ represents an alkoxy group; n represents an integer of from 1 to 4; m is an integer of from 1 to 3; l is an integer of from 1 to 3; $R_5$ represents an alkyl group or an aryl group; $R_6$ represents hydrogen, a halogen atom, an alkyl group, an alkoxy group or an aryl group; and a is an integer of from 1 to 5; and b is an integer of from 1 to 5.

DETAILED DESCRIPTION OF THE INVENTION

The magenta couplers which can be used in the color photographic light-sensitive material of the present invention are novel couplers belonging to a group of two-equivalent magenta couplers having an arylthio group at the coupling active position of a pyrazolone.

The magenta couplers which can be used in the present invention are described in more detail below.

In the general formulae (I) and (II), Ar represents a substituted phenyl group. The substituent for the phenyl group includes a halogen atom (for example, chlorine, bromine, fluorine, etc.), an alkyl group having from 1 to 22 carbon atoms (for example, a methyl group, an ethyl group, a tetradecyl group, a tert-butyl group, etc.), an alkoxy group having from 1 to 22 carbon atoms (for example, a methoxy group, an ethoxy group, an octyloxy group, a dodecyloxy group, etc.), an alkoxycarbonyl group having from 2 to 23 carbon atoms (for example, a methoxycarbonyl group, an ethoxycarbonyl group, a tetradecyloxycarbonyl group, etc.), or a cyano group.

X in the general formulae (I) and (II) represents a halogen atom (for example, chlorine, bromine, fluorine, etc.) or an alkoxy group having from 1 to 22 carbon atoms (for example, a methoxy group, an octyloxy group, a dodecyloxy group, etc.).

$R_1$ in the general formulae (I) and (II) represents hydrogen, a halogen atom (for example, chlorine, bromine, fluorine, etc.), an alkyl group (for example, a methyl group, a tert-butyl group, a 2-methanesulfonamidoethyl group, a tert-butanesulfonylethyl group, a tetradecyl group, etc.), an alkoxy group (for example, a methoxy group, an ethoxy group, a 2-ethylhexyloxy group, a tetradecyloxy group, etc.), an acylamino group (for example, an acetamido group, a benzamido group, a butanamido group, a tetradecanamido group, an α-(2,4-di-tert-amylphenoxy)acetamido group, an α-(2,4-di-tert-amylphenoxy)butyramido group, an α-(3-pentadecylphenoxy)hexanamido group, an α-(4-hydroxy-3-tertbutylphenoxy)tetradecanamido group, a 2-oxopyrrolidin-1-yl group, a 2-oxo-5-tetradecylpyrrolidin-1-yl group, an N-methyltetradecanamido group, etc.), a sulfonamido group (for example, a methanesulfonamido group, a benzenesulfonamido group, a p-toluenesulfonamido group, an octanesulfonamido group, a p-dodecylbenzenesulfonamido group, an N-methyltetradecanesulfonamido group, etc.), a sulfamoyl group (for example, an N-methylsulfamoyl group, an N-hexadecylsulfamoyl group, an N-[3-(dodecyloxy)propyl]sulfamoyl group, an N-[4-(2,4-di-tert-amylphenoxy)butyl]sulfamoyl group, an N-methyl-N-tetradecylsulfamoyl group, etc.), a carbamoyl group (for example, an N-methylcarbamoyl group, an N-octadecylcarbamoyl group, an N-[4-(2,4-di-tert-amylphenoxy)butyl]carbamoyl group, an N-methyl-N-tetradecylcarbamoyl group, etc.), a diacylamino group (for example, an N-succinimido group, an N-phthalimido group, a 2,5-dioxooxazolidinyl group, a 3-dodecyl-2,5-dioxo-1-hydantoinyl group, a 3-(N-acetyl-N-dodecylamino)succinimido group, etc.), an alkoxycarbonyl group (for example, a methoxycarbonyl group, a tetradecyloxycarbonyl group, a benzyloxycarbonyl group, etc.), an alkoxysulfonyl group (for example, a methoxysulfonyl group, an octyloxysulfonyl group, a tetradecyloxysulfonyl group, etc.), an aryloxysulfonyl group (for example, a phenoxysulfonyl group, a 2,4-di-tert-amylphenoxysulfonyl group, etc.), an alkanesulfonyl group (for example, a methanesulfonyl group, an octanesulfonyl group, a 2-ethylhexanesulfonyl group, a hexadecanesulfonyl group, etc.), an arylsulfonyl group (for example, a benzenesulfonyl group, a 4-nonylbenzenesulfonyl group, etc.), an alkylthio group (for example, an ethylthio group, a hexylthio group, a benzylthio group, a tetradecylthio group, a 2-(2,4-di-tert-amylphenoxy)ethylthio group, etc.), an arylthio (for example, a phenylthio group, a p-tolylthio group, etc.), an alkyloxycarbonylamino group (for example, an ethyloxycarbonylamino group, a benzyloxycarbonylamino group, a hexadecyloxycarbonylamino group, etc.), a ureido group (for example, an N-methylureido group, an N-phenylureido group, an N,N-dimethylureido group, an N-methyl-N-dodecylureido group, an N-hexadecylureido group, an N,N-dioctadecylureido group, etc.), an acyl group (for example, an acetyl group, a benzoyl group, an octadecanoyl group, a p-dodecanamidobenzoyl group, etc.), a nitro group, or a carboxy group. In the above-described substituents, the alkyl moieties thereof preferably have from 1 to 36 carbon atoms, and the aryl moieties thereof preferably have from 6 to 38 carbon atoms.

$R_2$ in the general formula (I) represents a halogen atom (for example, chlorine, bromine, etc.), a hydroxy group, an amino group (an unsubstituted or substituted amino group including an N-alkylamino group, an N,N-dialkylamino group, an N-anilino group, an N-alkyl-N-arylamino group, a heterocyclic amino group, etc., for example, an N-butylamino group, an N,N-dibutyl amino group, an N,N-dihexylamino group, an N-piperidino group, an N,N-bis(2-dodecyloxyethyl)amino group, an N-cyclohexylamino group, an N-phenylamino group, an N,N-bis(2-hexanesulfonylethyl)amino group, etc.), an alkyl group (including a straight chain or branched chain alkyl group, an aralkyl group, an alkenyl group, a cycloalkyl group, a cycloalkenyl group, for example, a methyl group, a butyl group, an octyl group, a dodecyloxy group, a benzyl group, a cyclopentyl group, a 2-methanesulfonylethyl group, a 3-phenoxypropyl group, etc.), an alkoxy group (for example, a methoxy group, a butoxy group, a benzyloxy group, a 2-ethylhexyloxy group, a dodecyloxy group, a 2-methanesulfonylethyl group, a 2-butanesulfonylethyl group, an isopropyloxy group, a 2-chloroethyl group, a 3-(2,4-di-tert-amylphenoxy)propyl group, a 2-(N-methylcarbamoyl)ethoxy group, a cyclopentyloxy group, a 2-ethoxytetradecyloxy group, a 4,4,4,3,3,2,2-heptafluorobutyloxy group, a 4-methanesulfonylbutoxy group, a 2-ethanesulfonamidoethyl group, etc.) or an aryl group (including an unsubstituted or substituted phenyl group having from 6 to 38 carbon atoms, an α- or β-naphthyl group, for example, a phenyl group, an α-naphthyl group, a β-naphthyl group, a 4-chlorophenyl group, a 4-tertbutylphenyl group, a methanesulfonamidophenyl group, a 2,4-dimethylphenyl group, etc.).

$R_3$ in the general formulae (I) and (II) represents an amino group (an unsubstituted or substituted amino group including an N-alkylamino group, an N,N-dialkylamino group, an N-anilino group, an N-alkyl-N-arylamino group, a heterocyclic amino group, for example, n N-butylamino group, an N,N-diethylamino group, an N-[2-(2,4-di-tert-amylphenoxy)ethyl]amino group, an N,N-dibutylamino group, an N-piperidino group, an N,N-bis(2-dodecyloxyethyl)amino group, an N-cyclohexylamino group, an N,N-dihexylamino group, an N-phenylamino group, a 2,4-di-tert-amylphenylamino group, an N-(2-chloro-5-tetradecanamidophenyl)amino group, an N-methyl-N-phenylamino group, an N-(2-pyridyl)amino group, etc.), an acylamino group (for example, an acetamido group, benzamido group, a tetradecanamido group, a (2,4-di-tert-amylphenoxy)acetamido group, a 2-chlorobenzamido group, a 3-pentadecylbenzamido group, a 2-(2-methanesulfonamidophenoxy)dodecanamido group, a 2-(2-chlorophenoxy)tetradecanamido group, etc.), a ureido group (for example, a methylureido group, a phenylureido group, a 4-cyanophenylureido group, etc.), an alkoxycarbonylamino group (for example, a methoxycarbonylamino group, a dodecyloxycarbonylamino group, a 2-ethylhexyloxycarbonylamino group, etc.), an imido group (for example, an N-succinimido group, an N-phthalimido group, an N-hydantoinyl group, a 5,5-dimethyl-2,4-dioxooxazol-3-yl group, an N-(3-octadecenylsuccinimido group, etc.), a sulfonamido group (for example, a methanesulfonamido group, an octanesulfonamido group, a benzenesulfonamido group, a 4-chlorobenzenesulfonamido group, a 4-dodecylbenzenesulfonamido group, an N-methyl-N-benzenesulfonamido group, a 4-dodecyloxybenzenesulfonamido group, a hexadecanesulfonamido group, etc.), a sulfamoylamino group (for example, an N-octylsulfamoylamino group, an N,N-dipropylsulfamoylamino group, an N-ethyl-N-phenylsulfamoylamino group, an N-(4-butyloxy)sulfamoylamino group, etc.), a nitro group, an alkoxycarbonyl group (for example, a methoxycarbonyl group, a butoxycarbonyl group, a dodecyloxycarbonyl group, a benzyloxycarbonyl group, etc.), a carbamoyl group (for example, an N-octylcarbamoyl group, an N,N-dibutylcarbamoyl group, an N-phenylcarbamoyl group, an N-[3-(2,4-di-tert-amylphenoxy)propyl]carbamoyl group, etc.), an acyl group (for example, an acetyl group, a benzoyl group, a hexanoyl group, a 2-ethylhexanoyl group, a 2-chlorobenzoyl group, etc.), a cyano group, or an alkylthio group (for example, a dodecylthio group, 2-ethylhexylthio group, a benzylthio group, a 2-oxocyclohexylthio group, a 2-(ethyltetradecanoate)thio group, a 2-(dodecylhexanoate)thio group, a 3-phenoxypropylthio group, a 2-dodecanesulfonylethylthio group, etc.).

$R_4$ in the general formula (I) represents hydrogen, a hydroxy group, or a halogen atom, an alkyl group, an alkoxy group, or an aryl group, each as defined for $R_2$ above. At least one of $R_2$ and $R_4$ represents an alkoxy group.

In the general formula (II), $R_5$ represents an alkyl group or an aryl group, each as defined for $R_2$ above, and $R_6$ represents hydrogen, or a halogen atom, an alkyl group, an alkoxy group or an aryl group, each as defined for $R_2$ above.

Of the compounds represented by the general formula (I) or (II), preferred compounds can be represented by the following general formula (III):

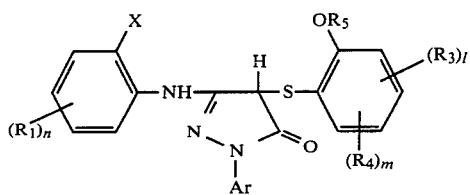

wherein Ar, X, $R_1$, $R_3$, $R_4$, $R_5$, l, m and n each has the same meaning as defined above.

Particularly preferred compounds can be represented by the following general formula (IV):

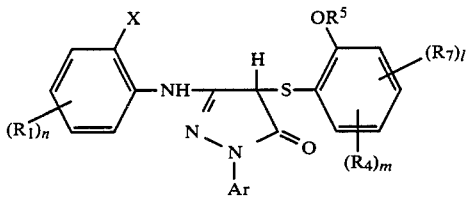

wherein Ar, X, $R_1$, $R_4$, $R_5$, l, m and n each has the same meaning as defined above and $R_7$ represents a substituent which is bonded through a nitrogen atom selected from the substituents as defined for $R_3$, i.e., an amino group, an acylamino group, a ureido group, an alkoxycarbonylamino group, an imido group, a sulfonamido group, a sulfamoylamino group or a nitro group.

An amount of the coupler used according to the present invention is preferably from about $2 \times 10^{-3}$ mol to about $5 \times 10^{-1}$ mol, particularly from $1 \times 10^{-2}$ mol to $5 \times 10^{-1}$ mol, per mol of silver in a silver halide emulsion layer.

Specific examples of the two-equivalent magenta couplers according to the present invention are set forth below, but the present invention is not to be construed as being limited to these compounds.

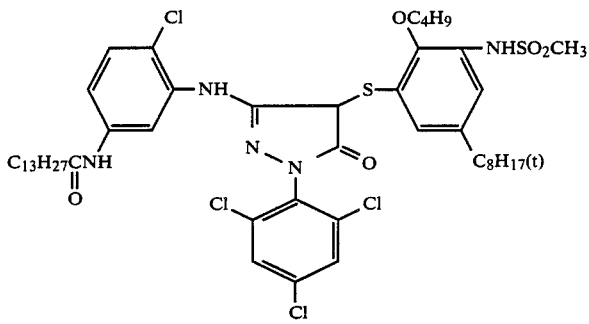

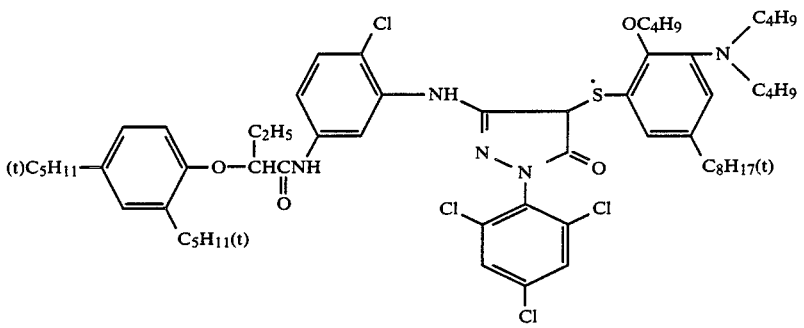

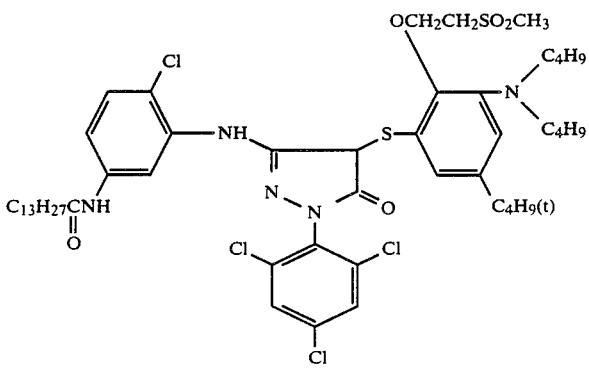

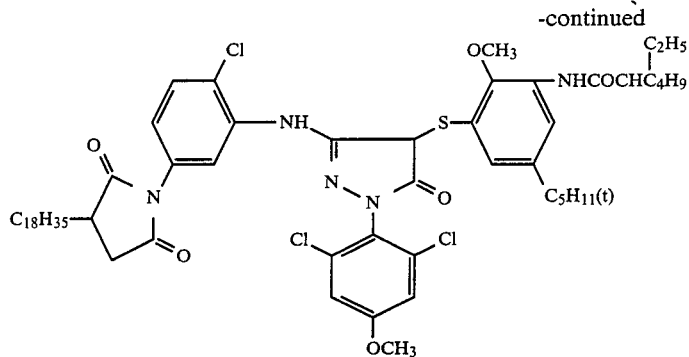
(4)
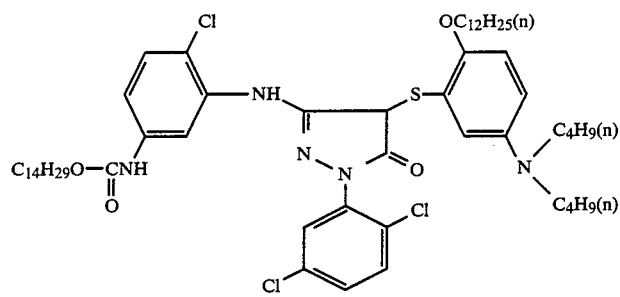
(5)
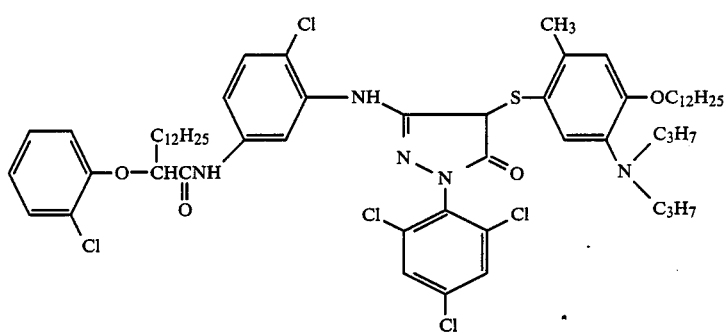
(6)
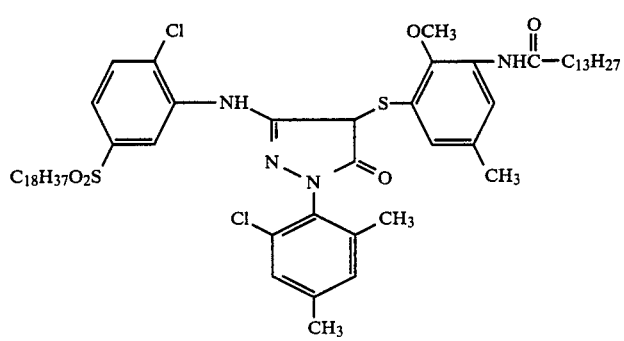
(7)
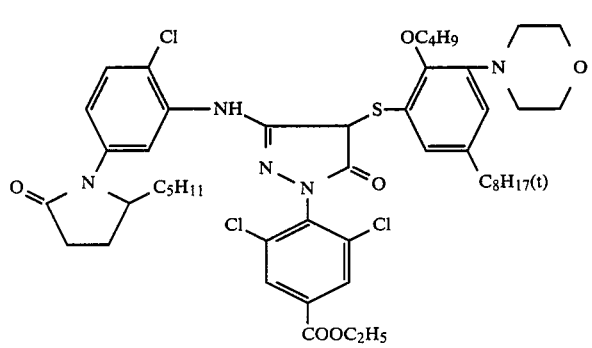
(8)

-continued
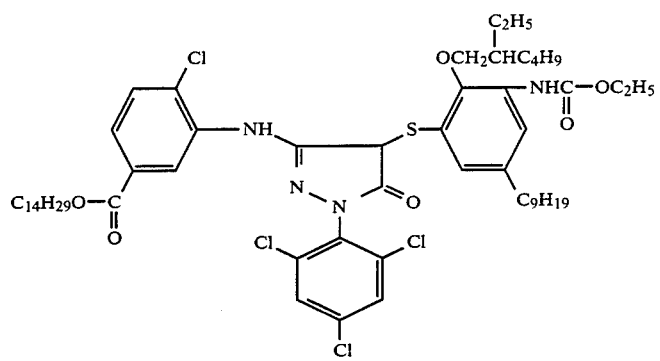
(9)
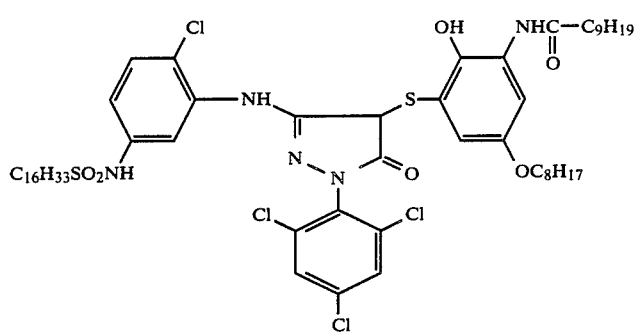
(10)
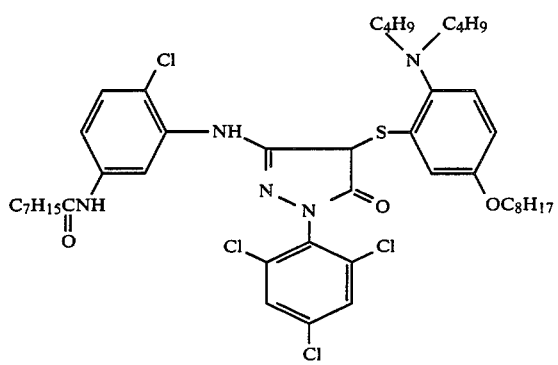
(11)
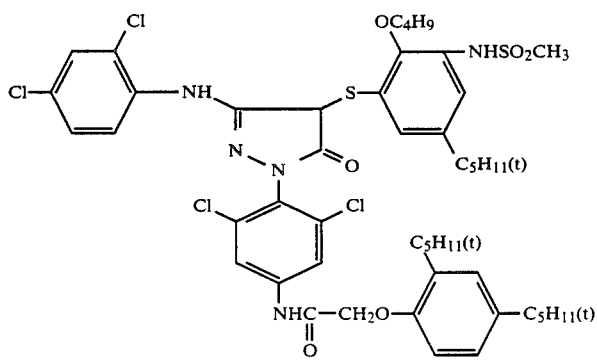
(12)

-continued
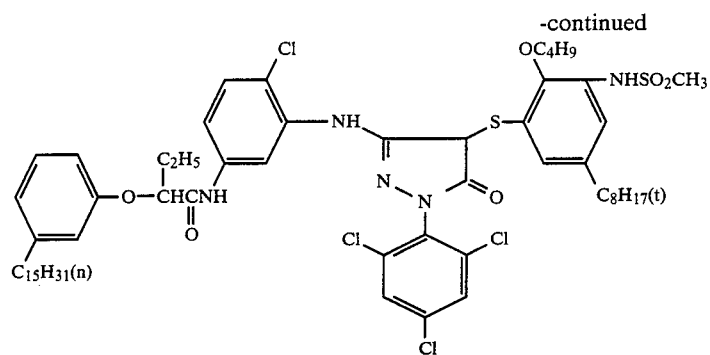 (13)
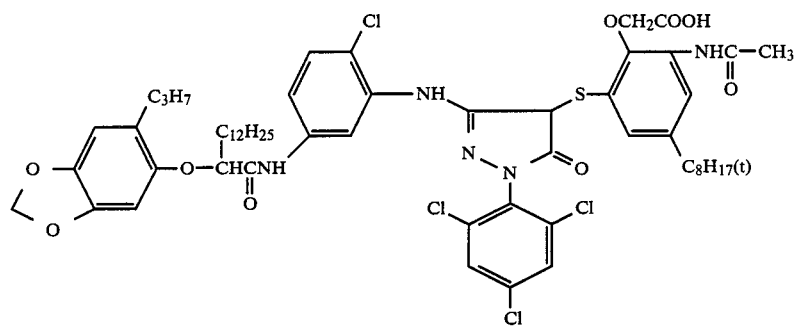 (14)
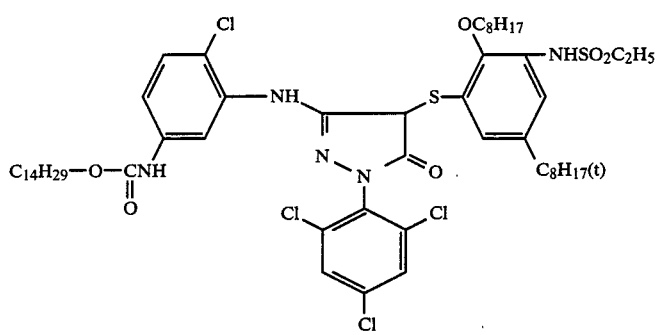 (15)
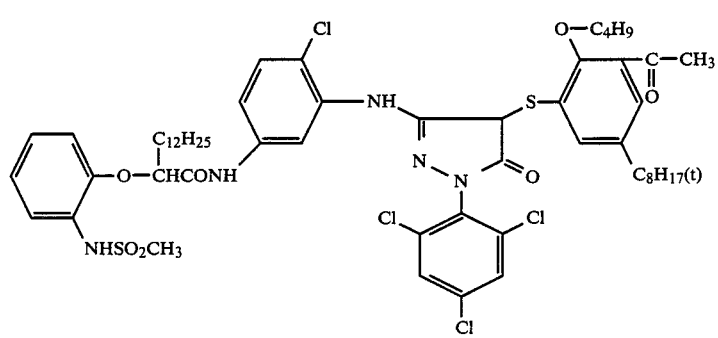 (16)
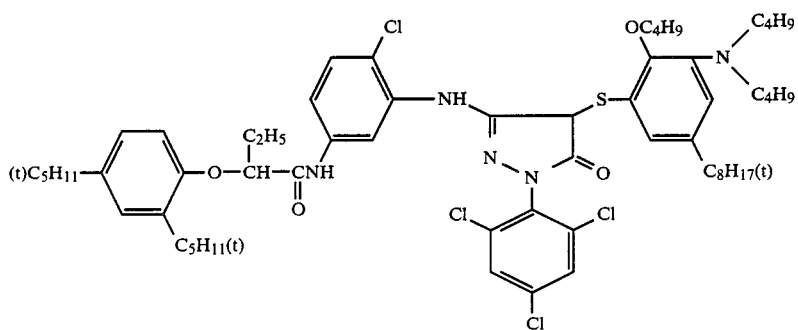 (17)

-continued
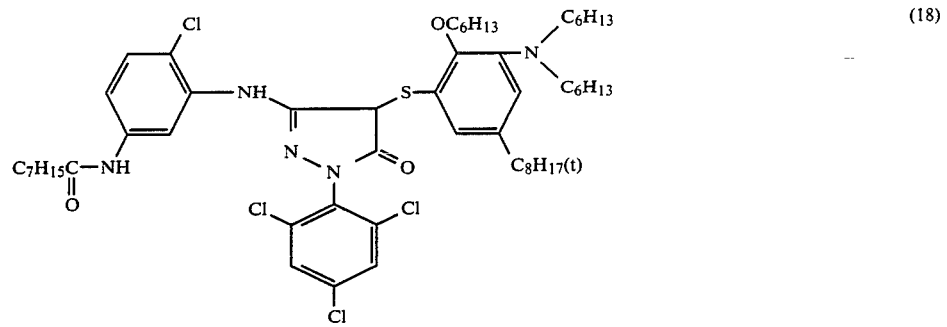 (18)
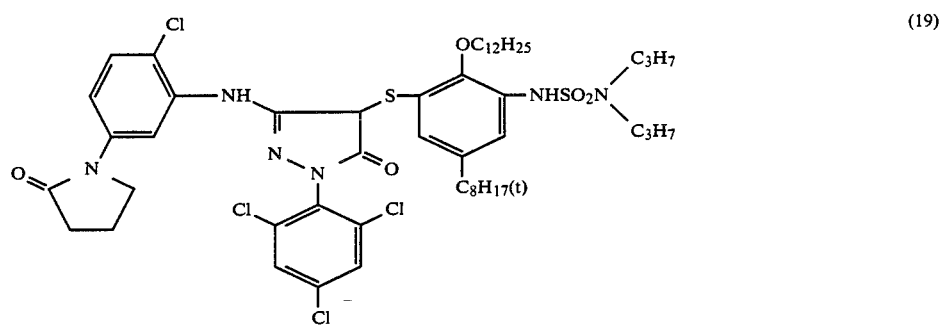 (19)
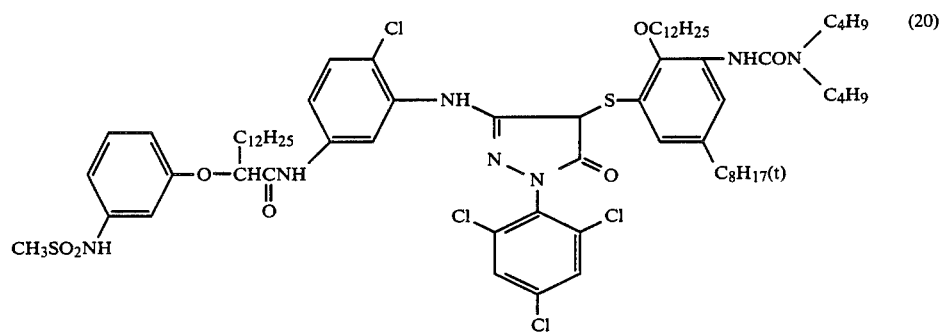 (20)
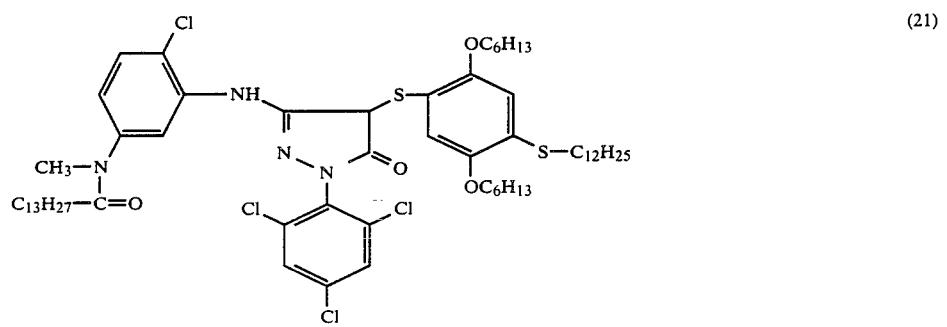 (21)

-continued
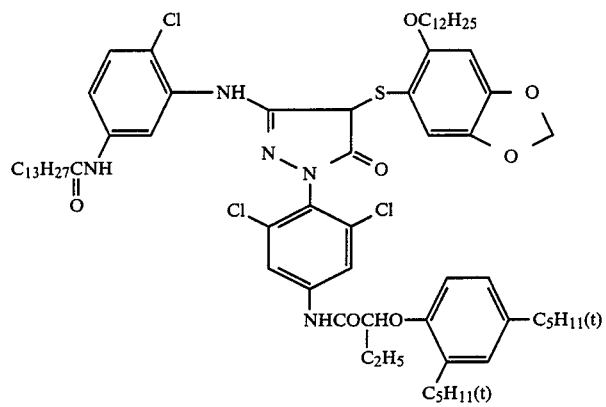 (22)
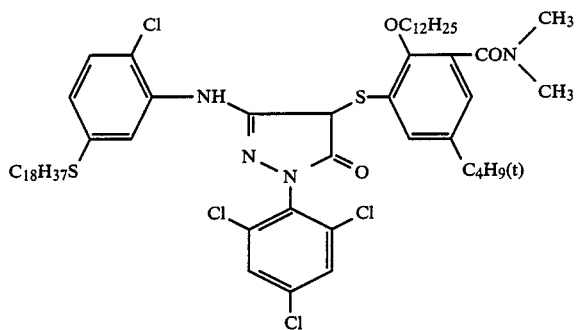 (23)
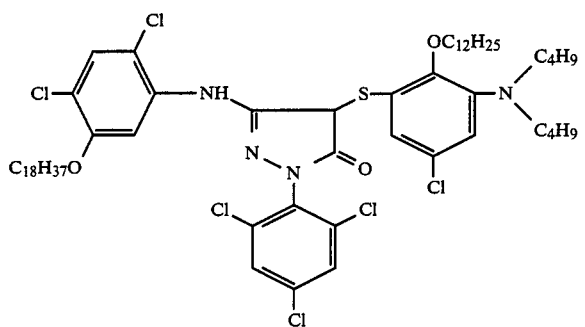 (24)
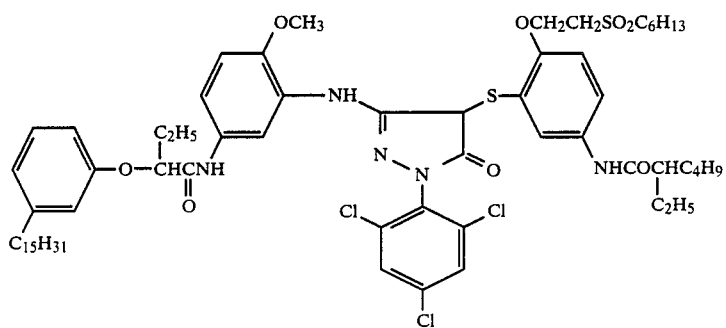 (25)

-continued
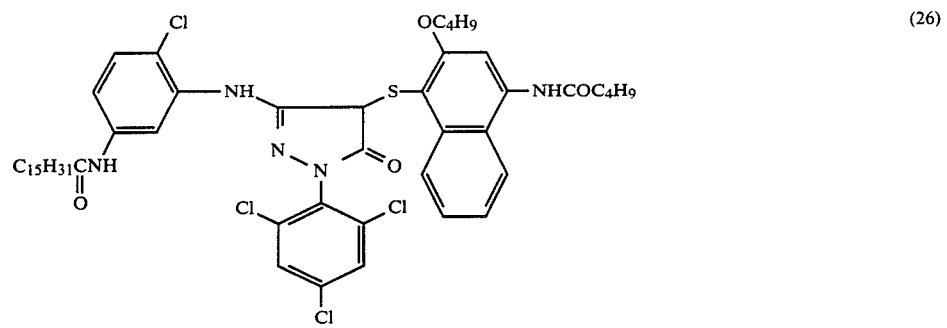 (26)
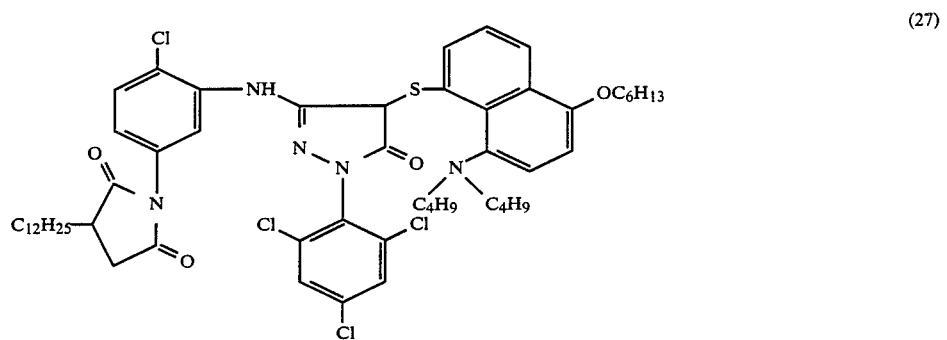 (27)
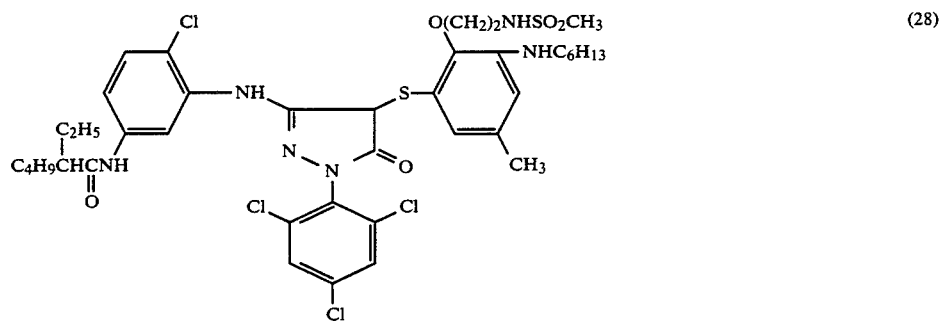 (28)
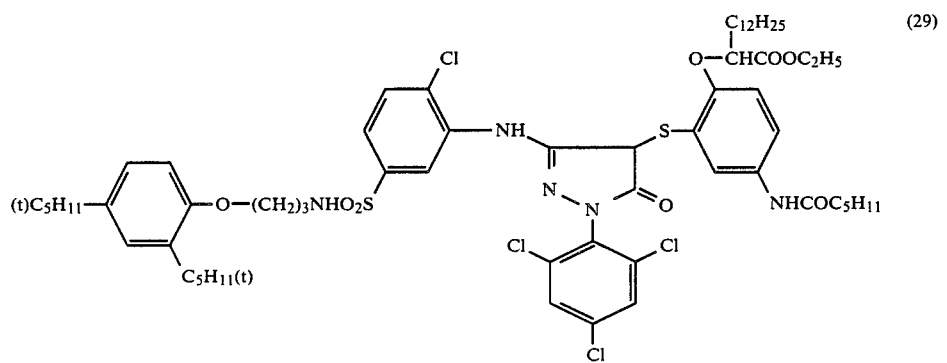 (29)

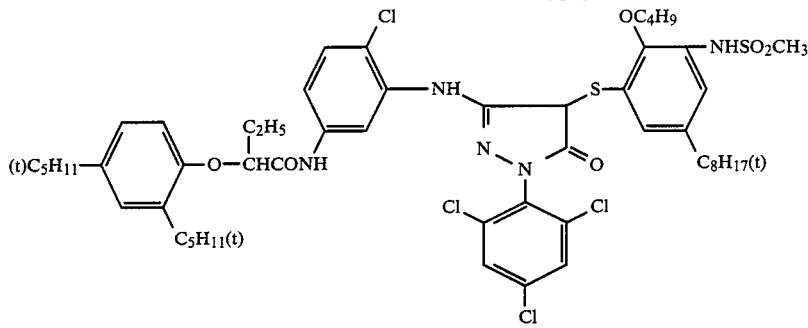

(30)

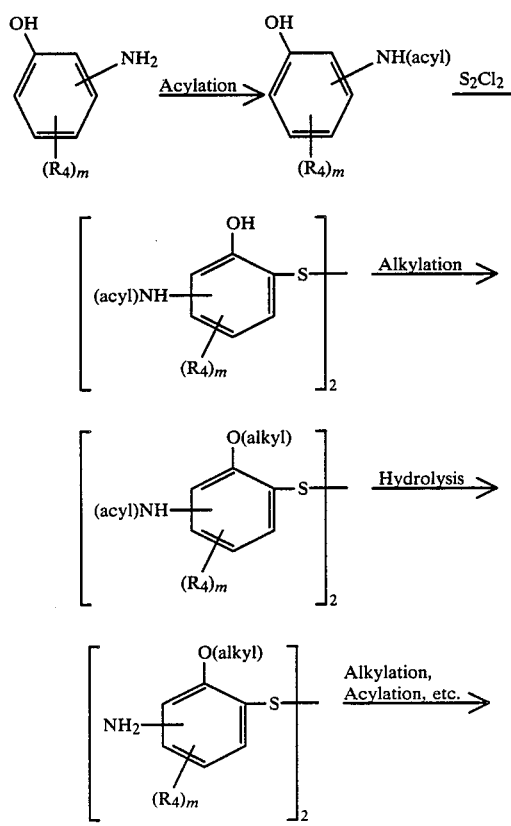

The magenta couplers which can be used in the present invention can be synthesized by the method described in Japanese Patent Application (OPI) No. 35858/82 using phenol derivatives or naphthol derivatives both of which are commercially available or can be synthesized by known methods. However, it is generally difficult to synthesize an arylthio group having a substituent containing a nitrogen atom bonded to the aromatic ring. Therefore, a method of synthesizing a diaryl disulfide having a substituent with a nitrogen atom bonded to the aryl group according to the present invention hereinafter is illustrated.

In the above-described formulae, $R_4$ and m each has the same meaning as defined above, and $R_8$ represents a substituent which is bonded to the phenyl group through a nitrogen atom.

Typical examples of synthesizing the magenta coupler according to the present invention are specifically set forth below. Unless otherwise indicated, all parts, percents, ratios and the like are by weight.

SYNTHESIS EXAMPLE 1

Synthesis of Coupler (1)

Reaction Scheme of Synthesis

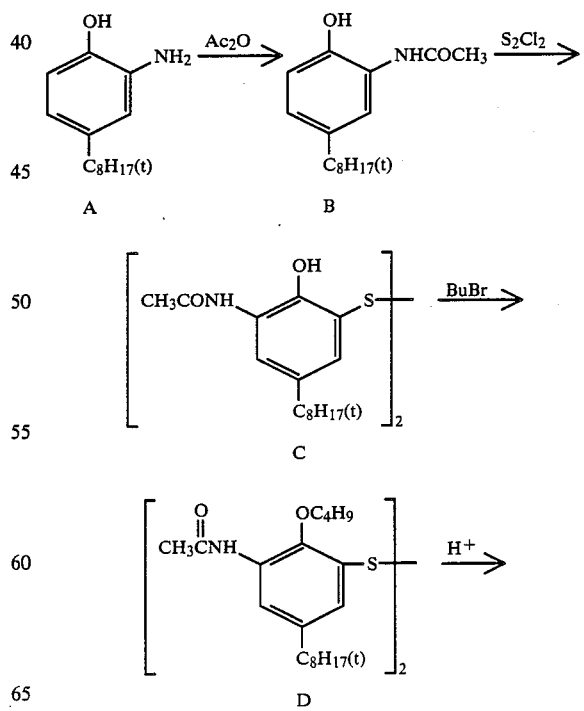

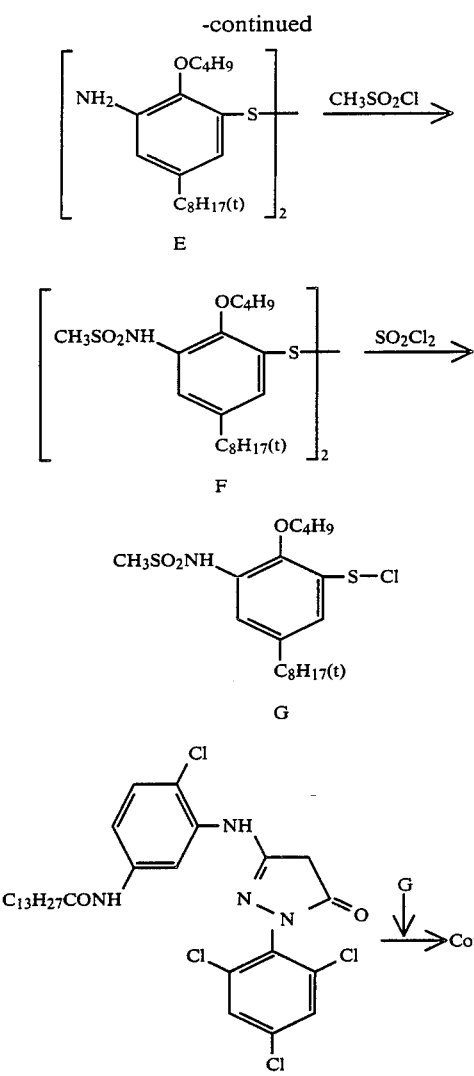

Step (a): Synthesis of Intermediate F

2-Amino-4-tert-octylphenol was refluxed by heating in a mixture of acetonitrile and acetic anhydride to synthesize Intermediate B having the melting point of 176° to 177° C. in a yield of 70%. 26.3 g of 2-acetamido-4-tert-octylphenol thus obtained was dissolved in 200 ml of chloroform, the solution was cooled to 0° to 5° C. to which was added 8.1 g of sulfur monochloride ($S_2Cl_2$) and the mixture was stirred for 2 hours. Water was added to the reaction solution, and the chloroform layer was thoroughly washed with water and then concentrated. The residue was dissolved in 50 ml of dimethylformamide without purification and isolation, to the solution were added 16.6 g of anhydrous potassium carbonate and 23 g of butyl bromide and the mixture was heated at 100° C. for 3 hours. After the reaction, 300 ml of ethyl acetate and 200 ml of water were added to the reaction mixture and extracted. The ethyl acetate layer was concentrated and the residue was crystallized from acetonitrile to obtain 15.8 g of Intermediate D having the melting point of 150° to 153° C. 15.8 g of Intermediate D thus obtained was dissolved in a mixture of 100 ml of ethanol and 10 ml of 6N hydrochloric acid and the mixture was stirred at 40° to 50° C. for 1 hour whereby the acetyl group of Intermediate D was quantitatively hydrolized. The reaction solution was poured into ice water and the precipitate thus formed was collected by filtration and dried to obtain 14 g of Intermediate E. 14 g of Intermediate E thus obtained was dissolved in 100 ml of pyridine, to the solution was added 5.7 g of methanesulfonyl chloride in a nitrogen atmosphere and the mixture was stirred at room temperature for 2 hours. The reaction solution was poured into ice water, the oily product thus precipitated was separated by decantation and dissolved in 200 ml of ethyl acetate. The solution was thoroughly washed with an aqueous acidic solution of acetic acid. The ethyl acetate was concentrated and the residue was crystallized from a mixture of hexane and ethyl acetate to obtain 9.3 g of Intermediate F having a melting point of 102° to 103° C.

Step (b): Synthesis of Coupler (1)

According to the method as described in Japanese Patent Application (OPI) No. 35858/82, 7.74 g of Intermediate F obtained in Step (a) above was dissolved in 30 ml of methylene chloride and to the solution was added dropwise 2.7 g of sulfuryl chloride while cooling at 0° to 10° C. After the completion of the dropwise addition, the mixture was stirred for 30 minutes and concentrated by distilling off the solvent to a half of the original amount. To the residue was gradually added dropwise a solution containing 12 g of 1-(2,4,6-trichlorophenyl)-3-(2-chloro-5-tetradecanamidoanilino)-5-oxo-2-pyrazoline dissolved in 50 ml of dimethylformamide. After the completion of the dropwise addition, the reaction solution was heated at 50° to 60° C. for 2 hours with stirring. Then the solution was cooled, extracted with ethyl acetate and the ethyl acetate layer was concentrated. The resulting residue was crystallized from benzene to obtain 18.5 g of Coupler (1) having a melting point of 176° to 177° C.

SYNTHESIS EXAMPLE 2

Synthesis of Coupler (30)

In the same manner as described in Synthesis Example 1 except using Intermediate F as described in Synthesis Example 1 and 1-(2,4,6-trichlorophenyl)-3-[2-chloro-5-{α-(2,4-di-tert-acylphenoxy)-butyramido}anilino]-5-oxo-2-pyrazoline, Coupler (30) having a melting point of 163° to 166° C. was obtained.

The magenta couplers according to the present invention can be used by dissolving them in a solvent having a high boiling point.

Any known solvent can be used as the above-described solvent having a high boiling point, particularly an organic solvent having a boiling point of not less than about 180° C. For example, a phthalic acid alkyl ester (e.g., dibutyl phthalate, dioctyl phthalate, etc.), a phosphoric acid ester (e.g., diphenyl phosphate, triphenyl phosphate, tricresyl phosphate, dioctylbutyl phosphate, etc.), a citric acid ester (e.g., tributyl acetylcitrate, etc.), a benzoic acid ester (e.g., octyl benzoate, etc.), an alkylamide (e.g., diethyl laurylamide, etc.), a fatty acid ester (e.g., dibutoxyethyl succinate, dioctyl azelate, etc.), a trimesic acid ester (e.g., tributyl trimesate, etc.), etc., as described in U.S. Pat. No. 2,322,027 are preferably used. In particular, an alkyl phosphate (e.g., diphenyl phosphate, triphenyl phosphate, tricresyl phosphate, dioctyl butyl phosphate, etc.) is most preferred.

The couplers used in the present invention are not unduly limited, and may be freely selected from those known in the art. Oil-soluble couplers are preferably used in the present invention.

Examples of useful magenta couplers include a 5-pyrazolone type coupler, a pyrazolotriazole type coupler and an imidazopyrazole type coupler. Examples of yellow couplers include a benzoylacetanilide type compound and a pivaloylacetanilide type compound which have been found to be advantageously used in the practice of the present invention. Examples of useful cyan couplers include a phenol type compound and a naphthol type compound.

In addition, colored couplers, DIR couplers, and compounds which release a development inhibitor as development may be used together.

Two or more of the above-described couplers may be contained in the same layer. Two or more layers may contain the same compound.

A ratio of oil/coupler is preferably from 0.0 to about 2.0.

In order to incorporate the above-described couplers into a hydrophilic colloid layer, the method using the above-described organic solvent having a high boiling point as described in U.S. Pat. No. 2,322,027 can be employed, or they may be dissolved in an organic solvent having a boiling point of from about 30° to 150° C., for example, a lower alkyl acetate (e.g., ethyl acetate, butyl acetate, etc.), ethyl propionate, sec-butyl alcohol, methyl isobutyl ketone, $\beta$-ethoxyethyl acetate, methyl cellosolve acetate, etc., and then the solution is dispersed in a hydrophilic colloid. The above-described organic solvents having a high boiling point and the above-described organic solvents having a low boiling point may be used as mixtures, if desired.

Furthermore, the dispersing method using a polymeric material as described in Japanese Patent Publication No. 39853/76, Japanese Patent Application (OPI) No. 59943/76 can also be used.

When a coupler having an acid group, such as a carboxylic acid group, a sulfonic acid group, etc., is used, it can be incorporated in a hydrophilic colloid as an alkaline aqueous solution thereof.

A subbing layer for the photographic light-sensitive material of the present invention is a hydrophilic colloid layer comprising a hydrophilic polymer such as gelatin (a binder or a protective colloid for a photographic emulsion described hereinafter can also be used) and is usually provided by coating on a support. By the provision of the subbing layer, in general, adhesion to the photographic emulsion layer can be improved and halation may be prevented.

The color photographic light-sensitive material of the present invention can be applied to any known color photographic light-sensitive material as far as they are subjected to color development processing, for example, color papers, color negative films, color reversal films, etc. It is particularly preferred to apply to photographic light-sensitive materials for printing (for example, color papers, etc.).

The silver halide photographic emulsion used in the present invention can be prepared by using processes described in P. Glafkides, *Chimie et Physique Photographique* (published by Paul Montel Co., 1967); G. F. Duffin, *Photographic Emulsion Chemistry* (published by The Focal Press, 1966); V. L. Zelikman et al., *Making and Coating Photographic Emulsion* (published by The Focal Press, 1964); etc. Any of an acid process, neutral process or ammonia process may be used. Further, a single jet process, a double jet process, or a combination thereof can be used for reacting a soluble silver salt with a soluble halide.

A process for forming particles in the presence of excess silver ion (the so-called reverse mixing process) can also be used. One useful double jet process involves a process keeping the liquid phase for forming silver halide at a definite pAg, namely, the so-called controlled double jet process. According to this process, a silver halide emulsion having a regular crystal form and nearly uniform particle size can be obtained.

Two or more silver halide emulsions prepared separately may also be blended to use.

In the photographic emulsion layer of the photographic light-sensitive material of the present invention, any of silver bromide, silver iodobromide, silver iodochlorobromide, silver chlorobromide and silver chloride can be used as the silver halide.

In the step of formation of silver halide particles or the step of physical ripening thereof, a cadmium salt, a zinc salt, a lead salt, a thallium salt, an iridium salt or a complex salt thereof, a rhodium salt or a complex salt thereof, an iron salt or a complex salt thereof, etc., may be coexistent therewith.

The photographic emulsions used in the present invention may be spectrally sensitized by methine dyes or others. Examples of dyes used include a cyanine dye, a merocyanine dye, a complex cyanine dye, a complex merocyanine dye, a holopolar cyanine dye, a hemicyanine dye, a styryl dye and a hemioxonol dye. Particularly useful dyes can be selected from a cyanine dye, a merocyanine dye, and a complex merocyanine dye. In these dyes, it is possible to utilize any basic heterocyclic nucleus conventionally utilized for a cyanine dye. Namely, it is possible to utilize a pyrroline nucleus, an oxazoline nucleus, a thiazoline nucleus, a pyrrole nucleus, an oxazole nucleus, a thiazole nucleus, a selenazole nucleus, an imidazole nucleus, a tetrazole nucleus and a pyridine nucleus; the above-described nuclei to which an alicyclic hydrocarbon ring is fused; and the above described nuclei to which an aromatic hydrocarbon ring is fused, namely, an indolenine nucleus, a benzindolenine nucleus, an indole nucleus, a benzoxazole nucleus, a naphthoxazole nucleus, a benzothiazole nucleus, a naphthothiazole nucleus, a benzoselenazole nucleus, a benzimidazole nucleus, a quinoline nucleus, etc. These nuclei may have substituents on the carbon atoms thereof.

In the merocyanine dye and the complex merocyanine dye, it is possible to utilize, as a nucleus having a ketomethylene structure, a 5- or 6-membered heterocyclic nucleus such as a pyrazolin-5-one nucleus, a thiohydantoin nucleus, a 2-thioxazolidin-2,4-dione nucleus, a thiazolidin-2,4-dione nucleus, a rhodanine nucleus, a thiobarbituric acid nucleus, etc.

These sensitizing dyes may be used alone, but a combination of them may also be used. The combination of the sensitizing dyes is frequently used for the purpose of supersensitization. Representative examples thereof have been described in U.S. Pat. Nos. 2,688,545, 2,977,229, 3,397,060, 3,522,052, 3,527,641, 3,617,293, 3,628,964, 3,666,480, 3,672,898, 3,679,428, 3,703,377, 3,769,301, 3,814,609, 3,837,862, and 4,026,707, British Pat. Nos. 1,344,281 and 1,507,803, Japanese Patent Publication Nos. 4936/68 and 12375/78, Japanese Patent Application (OPI) Nos. 110618/77 and 109925/77.

The emulsion may contain a dye which does not have a spectral sensitization function and shows supersensitization together with the sensitizing dye, or a substance which does not substantially absorb visible rays and shows supersensitization together with the sensitizing dye. For example, the emulsion may contain an aminostilbene compound substituted with a nitrogen-containing heterocyclic group (for example, those described in U.S. Pat. Nos. 2,933,390 and 3,635,721), an aromatic organic acid-formaldehyde condensed product (for example, those described in U.S. Pat. No. 3,743,510), a cadmium salt, an azaindene compound, etc. Combinations as described in U.S. Pat. Nos. 3,615,613, 3,615,641, 3,617,295 and 3,635,721 are particularly useful.

The binder or protective colloid for the photographic emulsion is preferably gelatin, but other hydrophilic colloids may also be used.

For example, it is possible to use a protein such as a gelatin derivative, a graft polymer of gelatin with other polymers, albumin, casein, etc.; a saccharide, including a cellulose derivative such as hydroxyethyl cellulose, carboxymethyl cellulose, cellulose sulfate, etc., sodium alginate, a starch derivative, etc.; and a synthetic hydrophilic polymeric substance such as a homopolymer or a copolymer such as polyvinyl alcohol, polyvinyl alcohol partial acetal, poly-N-vinylpyrrolidone, polyacrylic acid, polymethacrylic acid, polyacrylamide, polyvinylimidazole, polyvinylpyrazole, etc.

The gelatin may be either lime-processed gelatin, acid-processed gelatin, or enzyme-processed gelatin, as described in *Bull. Soc. Sci. Phot. Japan,* No. 16, page 30 (1966).

The present invention can be applied to a multilayer multicolor photographic light-sensitive material comprising at least two layers having different spectral sensitivities on a support. The multilayer natural color photographic light-sensitive material generally has at least one red-sensitive emulsion layer, at least one green-sensitive emulsion layer, and at least one blue-sensitive emulsion layer on the support. The order of these layers may be suitably varied as occasion demands. Generally, the red-sensitive emulsion layer contains a cyan forming coupler, the green-sensitive emulsion layer contains a magenta forming coupler, and the blue-sensitive emulsion layer contains a yellow forming coupler. However, if desired, other combinations may be utilized.

In the photographic light-sensitive material produced according to the present invention, the hydrophilic colloid layer may contain a water-soluble dye as a filter dye or for other purposes such as prevention of irradiation. Examples of such dyes include an oxonol dyes, a hemioxonol dye, a styryl dye, a merocyanine dye, a cyanine dye, and an azo dye. Among them, an oxonol dye, a hemioxonol dye and a merocyanine dye are particularly useful.

In carrying out the present invention, known color fading preventing agents may be used. Further, such dye image stabilizers in the present invention may be used alone, or two or more of them may be used together. Examples of the known color fading preventing agents include compounds as described in U.S. Pat. Nos. 3,336,135, 3,432,300, 3,573,050, 3,574,627, 3,700,455, 3,764,337, 3,935,016, 3,982,944, 4,254,216 and 4,279,990, British Pat Nos. 1,347,556, 2,062,888, 2,066,975 and 2,077,455, Japanese Patent Application No. 205278/83, Japanese Patent Application (OPI) Nos. 152225/77, 17729/78, 20327/78, 145530/79, 6321/80, 21004/80, 24141/83 and 10539/84, and Japanese Patent Publication Nos. 31625/73 and 12337/79. An amount of these color fading preventing agents used is from 5 to 200 mol%, preferably from 20 to 100 mol%, based on the amount of couplers used according to the present invention.

The magenta couplers capable of releasing a sulfur atom exhibit a superior color forming property even in the presence of alkaline earth metal ions. However, these magenta couplers rarely form stains (increase in color density in unexposed areas) during development processing or during preservation after development processing. These stains deteriorate the brightness of white areas in the color image, form the color turbidity of the image areas and injure the visual sharpness of the images. Various additives are investigated in order to prevent the occurrence of stains and it is found that antioxidation agents and amines are effective. Preferred examples of the antioxidation agents include hydroquinones, aminophenols, gallic acid derivatives, ascorbic acid derivatives, spiroindane derivatives and 3-pyrazolone derivatives. Particularly preferred examples thereof include hydroquinones and/or spiroindane derivatives, which may be used alone or two or more of them may be used together.

The preferred examples of stain preventing agents or color turbidity preventing agents for 2-equivalent pyrazolone couplers used according to the present invention also include amines. These additives may be used alone or preferably may be used together with above-mentioned antioxidation agents. The examples of amines include in an order of preference N-substituted anilines as described in Japanese Patent Application (OPI) No. 105147/83, steric hindrance cyclic tertiary amines as described in Japanese Patent Application (OPI) No. 102231/83, N-substituted aminotriazines as described in Japanese Patent Application No. 92082 (corresponding to U.S. Ser. No. 614,091 filed on May 25, 1984) and tertiary alkylamines as described in Japanese Patent application No. 105501/83 (corresponding to U.S. Ser. No. 620,238 filed on June 13, 1985, now abandoned. The amines descrease activities of the pyrazolone-type couplers due to the salt-formation with the pyrazolone-type couplers in neutral condition. Further the antioxidation agents prevent aerial oxidation of couplers or leuco dyes and consequently restrain or decrease the occurrence of stains. An amount of the oxidation agents used according to the present invention is from 0.2 mol to 2 mol, preferably from 0.7 mol to 1.3 mol, per mol of couplers. An amount of the amines used according to the present invention is from 0.8 mol to 2.0 mol, preferably from 1.1 mol to 1.6 mol, per mol of couplers. These additives preferably may be used as co-emulsion with coupler.

In the photographic light-sensitive material prepared according to the present invention, it is preferred that the hydrophilic colloid layer contain an ultra violet absorbing agent. For example, it is possible to use a benzotriazole compound substituted with an aryl group (for example, those described in U.S. Pat. No. 3,533,794), a 4-thiazolidone compound (for example, those described in U.S. Pat. Nos. 3,314,794 and 3,352,681), a benzophenone compound (for example, those described in Japanese Patent Application (OPI) No. 2784/71), a cinnamic acid ester compound (for example, those described in U.S. Pat. Nos. 3,705,805 and 3,707,375), a butadiene compound (for example, those described in U.S. Pat No. 4,045,229), and a benzoxazole compound (for example, those described in U.S. Pat. No. 3,700,455). Further, it is possible to use those described in U.S. Pat. No. 3,499,762, European Pat. No. 0057160, *Research Disclosure*, Vol. 225, No. 22519 and Japanese Patent Application (OPI) No. 48535/79. A coupler having an ultra violet absorbing property (for example, an α-naphthol type cyan dye forming coupler) and a polymer having an ultra violet absorbing property may also be used. These ultra violet absorbing agents may be mordanted on a specified layer.

In the photographic light-sensitive material prepared according to the present invention, the photographic emulsion layer and other hydrophilic colloid layers may contain a whitening agent such as a stilbene, triazine, oxazole, or coumarin type compound. They may be water-soluble. Further, a water-insoluble whitening agent may be used in the form of a dispersion.

In the photographic light-sensitive material of the present invention, the photographic emulsion layer and other hydrophilic layers can be coated on a support or other layers using various known coating methods. A dip coating method, a roller coating method, a curtain coating method, an extrusion coating method, etc., can be employed for coating.

The photographic processing of the photographic light-sensitive material of the present invention can be carried out by any known process. Known processing solutions can be used. The processing temperature is selected, generally, from about 18° C. to about 50° C., but a temperature of lower than 18° C. or higher than 50° C. may be used. The development method selected is not limited, and any color development processings providing dye images can be employed as desired.

The color developing solution is generally composed of an alkaline aqueous solution containing a color developing agent. The color developing agent may be a known primary aromatic amine developing agent. Examples of these agents include a phenylenediamine (for example, 4-amino-N,N-diethylaniline, 3-methyl-4-amino-N,N-diethylaniline, 4-amino-N-ethyl-N-β-hydroxyethylaniline, 3-methyl-4-amino-N-ethyl-N-β-hydroxyethylaniline, 3-methyl-4-amino-N-ethyl-N-β-methanesulfonamidoethylaniline, 4-amino-3-methyl-N-ethyl-N-β-methoxyethylaniline, etc.).

In addition, those described in L. F. A. Mason, *Photographic Processing Chemistry* (Focal Press, 1966), pages 226 to 229, U.S. Pat. Nos. 2,193,015 and 2,592,364, Japanese Patent Application (OPI) No. 64933/73, etc., may be used.

The color developing solution may contain a pH buffering agent such as a sulfite, a carbonate, a borate or a phosphate of an alkali metal, and a development restrainer or an antifogging agent such as a bromide, an iodide, an organic antifogging agent, etc. If necessary, it may contain a water softener, a preservative such as hydroxylamine, an organic solvent such as benzyl alcohol or diethylene glycol, a development accelerator such as polyethylene glycol, a quaternary ammonium salt or an amine, a dye forming coupler, a competitive coupler, a fogging agent such as sodium borohydride, a viscosity imparting agent, a polycarboxylic acid type chelating agent as described in U.S. Pat. No. 4,083,723, and an antioxidant as described in West German Patent Application (OLS) No. 2,622,950, etc.

After carrying out the color development, the photographic emulsion layers are generally subjected to bleaching. The bleaching may be carried out simultaneously with fixing or may be carried out separately. The bleaching agent may be a compound of a polyvalent metal such as iron (III), cobalt (III), chromium (VI) or copper (II), etc., a peracid, a quinone or a nitroso compound. For example, it is possible to use a ferricyanide, a bichromate, and an organic complex salt of iron (III) or cobalt (III), for example, a complex salt of an aminopolycarboxylic acid such as ethylenediaminetetraacetic acid, nitrilotriacetic acid or 1,3-diamino-2-propanol tetraacetic acid, etc., or an organic acid such as citric acid, tartaric acid, malic acid, etc.; a persulfate; a permanganate; nitrosophenol; etc. Among them, potassium ferricyanide, (ethylenediaminetetraacetato)iron (III) sodium complex and (ethylenediaminetetraacetato)iron (III) ammonium complex are particularly useful. (Ethylenediaminetetraacetato)iron (III) complexes are useful for both a bleaching solution and a mono-bath bleach-fixing solution.

To the bleaching solution or the bleach-fixing solution, it is possible to add a bleaching accelerator, a thiol compound, and various other additives.

In order to accelerate color development, a color developing agent or a derivative thereof may be previously incorporated into the photographic light-sensitive material. For example, it may be incorporated as a metal salt or a Schiff's base. Specific examples of compounds which can be used are described in U.S. Pat. Nos. 3,342,559 and 3,719,492, *Research Disclosure*, No. 15159 (1976). Further, a developing agent such as a hydroquinone, a 3-pyrazolidone derivative or an aminophenol derivative, etc., may be incorporated into the photographic light-sensitive material.

The present invention is illustrated in greater detail by reference to the following examples, but the present invention is not to be construed as being limited thereto.

EXAMPLE 1

On a paper support both surfaces of which were laminated with polyethylene was coated a coating solution comprising silver chlorobromide (silver bromide: 90 mol%; coating amount of silver: 350 mg/m$^2$), gelatin (2,000 mg/m$^2$) and a dispersion of a 4-equivalent magenta coupler, i.e., Cp-A (400 mg/m$^2$) and 2,5-di-tert-octyl hydroquinone (40 mg/m$^2$) together with a coupler solvent, i.e., o-cresyl phosphate (530 mg/m$^2$). On this emulsion layer was coated a gelatin protective layer (1,000 mg/m$^2$) to prepare Sample 1.

In the same manner as described in Sample 1 above except that using an equimolar amount of comparative 2-equivalent couplers Cp-B, Cp-C and Cp-D and the 2-equivalent magenta couplers according to the present invention, i.e., Couplers (1), (2), (3), (5), (11) and (30) in place of the 4-equivalent magenta coupler and reducing the coating amount of silver halide to one half of that in Sample 1, Samples 2 to 10 were prepared, respectively.

These samples were exposed to light through an optical wedge and processed according to the following steps:

| Processing Step (33° C.) | |
|---|---|
| Color Development | 3 min 30 sec |
| Bleach-Fixing | 1 min 30 sec |
| Washing with Water | 3 min |
| Drying (at 50° C. to 80° C.) | 2 min |

The composition of each processing solution used in the above processing was set forth below:

|  | Fresh Solution | Replenisher |
| --- | --- | --- |
| Color Developing Solution |  |  |
| Benzyl Alcohol | 12 ml | 15 ml |
| Diethylene Glycol | 5 ml | 5 ml |
| Potassium Carbonate | 25 g | 25 g |
| Sodium Chloride | 0.1 g | — |
| Sodium Bromide | 0.5 g | — |
| Anhydrous Sodium Sulfite | 2 g | 2.5 g |
| Hydroxylamine Sulfate | 2 g | 3.0 g |
| Fluorescent Whitening Agent | 1 g | 1.2 g |
| N—Ethyl-N—β-methanesul-fonamidoethyl-3-methyl-4-aminoaniline Sulfate | 4 g | 6.0 g |
| Water to make | 1 liter | 1 liter |
| pH | 10.2 | 10.5 |
| Bleach-Fixing Solution |  |  |
| Ammonium Thiosulfate | 124.5 g | 130 g |
| Sodium Metabisulfite | 13.3 g | 17.0 g |
| Anhydrous Sodium Sulfite | 2.7 g | 3.0 g |
| Iron (III) Ammonium Ethylenediaminetetraacetate | 65 g | 70 g |
| pH | 6.7–6.8 | 6.7–6.8 |
| Water to make | 1 liter | 1 liter |

The development processing was carried out using a conventional roller transportation type developing machine and the processing solutions the composition of which had become almost equilibrium condition (i.e., invariable condition) by processing continuously under the replenishment procedure wherein the replenisher for bleach-fixing solution had been replenished to the processing solution at a rate of 327 ml per m² of color paper processed until the total amount of the replenisher (i.e., the total amount of the processing solution overflowed from the bleach-fixing processing tank) had become twice in volume of the bleach-fixing processing tank.

Then, the magenta reflective densities in the maximum density area (Dmax area) and in the unexposed area were measured using a Fuji type automatic recording densitometer. The results thus obtained are set forth in Table 1 below.

TABLE 1

|  |  | Magenta Density | |
| --- | --- | --- | --- |
| Sample No. | Magenta Coupler | Dmax Area | Unexposed Area |
| 1 (Comparison) | Cp-A | 2.12 | 0.05 |
| 2 (Comparison) | Cp-B | 2.01 | 0.35 |
| 3 (Comparison) | Cp-C | 2.30 | 0.21 |
| 4 (Comparison) | Cp-D | 2.11 | 0.20 |
| 5 (Present Invention) | (1) | 2.29 | 0.05 |
| 6 (Present Invention) | (2) | 2.31 | 0.06 |
| 7 (Present Invention) | (3) | 2.28 | 0.05 |
| 8 (Present Invention) | (5) | 2.32 | 0.06 |
| 9 (Present Invention) | (11) | 2.31 | 0.06 |
| 10 (Present Invention) | (30) | 2.30 | 0.05 |

The structural formulae of Cp-A to Cp-D were as follows:

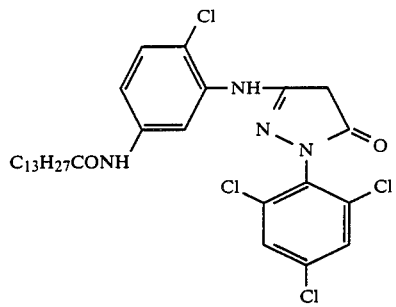

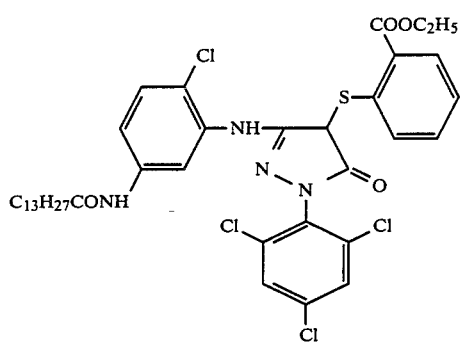

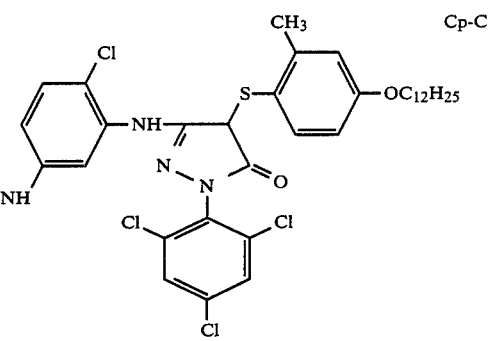

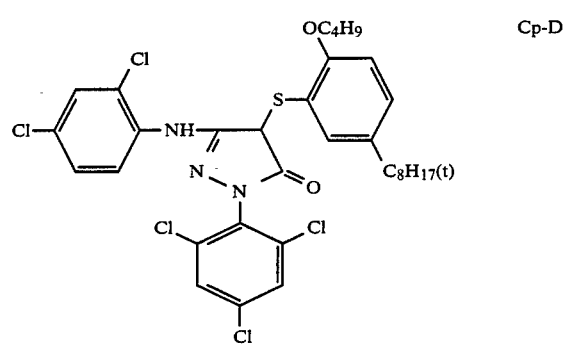

From the results shown in Table 1 above, it is apparent that Samples 2 to 10 containing the so-called 2-equivalent couplers exhibit a sufficiently high color density in spite of reducing the coating amount of silver halide to one half of that in Sample 1, as compared with Sample 1 wherein the so-called 4-equivalent coupler is used. However, in Samples 2 to 4 containing known 2-equivalent magenta couplers for comparison, magenta stains are formed in the unexposed area with processing under running conditions as shown in this example, and the photographic materials are not fit for practical use. By contrast, in Samples 5 to 10 wherein magenta couplers according to the present invention are used the occurrence of magenta stains is substantially prevented and excellent photographic properties are obtained.

The color forming property of coupler of the present invention was not affected even if the pH of the color developing solution varied within a range of about ±0.15.

EXAMPLE 2

On a paper support both surfaces of which were laminated with polyethylene were coated a first layer (undermost layer) to a sixth layer (uppermost layer) as shown below in order to prepare a multilayer color photographic light-sensitive material which is designated Sample A. In the Table below the coating amounts are set forth in mg/m².

| | |
|---|---|
| Sixth Layer: (protective layer) | Gelatin (1,500 mg/m²) |
| Fifth Layer: (red-sensitive layer) | Silver chlorobromide emulsion (silver bromide: 50 mol %; silver: 250 mg/m²) Gelatin (1,500 mg/m²) Cyan coupler*¹ (500 mg/m²) Coupler solvent*² (250 mg/m²) |
| Fourth Layer: (ultra violet absorbing layer) | Gelatin (1,200 mg/m²) Ultra violet absorbing agent*³ (700 mg/m²) Ultra violet absorbing agent solvent*² (250 mg/m²) |
| Third Layer: (green-sensitive layer) | Silver chlorobromide emulsion (silver bromide: 70 mol %; silver: 350 mg/m²) Gelatin (1,500 mg/m²) Magenta coupler*⁴ (400 mg/m²) Coupler solvent*⁵ (400 mg/m²) |
| Second Layer: (interlayer) | Gelatin (1,000 mg/m²) |
| First Layer: (blue-sensitive layer) | Silver chlorobromide emulsion (silver bromide: 80 mol %; silver: 350 mg/m²) Gelatin (1,500 mg/m²) Yellow coupler*⁶ (500 mg/m²) Coupler solvent*² (500 mg/m²) |
| Support: | Paper support both surfaces of which were laminated with polyethylene [white pigment (TiO₂, etc.) and bluish dye (ultramarine blue, etc.) are incorporated into the polyethylene layer of the first layer side] |

*¹Cyan coupler: 2-{α-(2,4-Di-tert-amylphenoxy)butan-amido}-4,6-dichloro-5-methyl-phenol
*²Coupler solvent: Trinonyl phosphate
*³Ultra violet absorbing agent: 2-(2-Hydroxy-3-sec-butyl-5-tertbutyl-phenyl)benzotriazole
*⁴Magenta coupler: 1-(2,4,6-trichlorophenyl)-3-(2-chloro-5-tetradecanamido)anilino-2-pyrazolin-5-one
*⁵Coupler solvent: Tri-o-cresyl phosphate
*⁶Yellow coupler: α-pivaloyl-α-(2,4-dioxo-5,5-di-methyloxazolidin-3-yl)-2-chloro-5-[α-(2,4-di-tert-amylphenoxy)butan-amido]acetanilide Samples B to G were prepared in the same manner as described in Sample A except that the couplers are set forth in Table 2 below as a magenta coupler and 175 mg/m² of the silver chlorobromide emulsion were used in the third layer.

These samples were exposed to green light through an optical wedge and subjected to the same processing steps as described in Example 1. The magenta reflective densities in the maximum density area (Dmax area) and in the unexposed area and the magenta densities were measured.

Further, these samples obtained by the development processing described above were subjected to a fading test for 5 days using a xenon fading tester (200,000 lux) and the magenta densities after the fading test were measured. The results thus obtained are shown in Table 2 below.

TABLE 2

| Sample No. | Magenta Coupler | Coating Amount (mg/m²) | Magenta Density Dmax Area | Magenta Density Unexposed Area | Density after* Fading Test |
|---|---|---|---|---|---|
| A (Comparison) | Cp-A | 400 | 2.35 | 0.07 | 0.74 |
| B (Comparison) | Cp-B | 515 | 2.29 | 0.40 | 0.25 |
| C (Comparison) | Cp-C | 600 | 2.37 | 0.31 | 0.76 |
| D (Comparison) | Cp-D | 465 | 2.36 | 0.29 | 0.08 |
| E (Present Invention) | (1) | 650 | 2.38 | 0.08 | 0.81 |
| F (Present Invention) | (3) | 675 | 2.37 | 0.07 | 0.85 |
| G (Present Invention) | (30) | 675 | 2.38 | 0.08 | 0.83 |

*Density after the xenon fading test at the area having the initial density of 1.0.

From the results shown in Table 2 above, it is apparent that Samples E, F and G wherein the 2-equivalent magenta coupler according to the present invention are used have sufficiently high color densities in spite of reducing the coating amount of silver halide to one half in the third layer, and do not exhibit the magenta stain in the unexposed areas which are observed in Samples B, C and D wherein known 2-equivalent magenta couplers are used, even under running conditions as described in this example. Further, it is clear that these samples of the present invention have the same level of light fastness as Samples C and D using the couplers which are known to posess the highest degree of light-fastness.

While the invention has been described in detail and with reference to specific embodiments thereof, it will be apparent to one skilled in the art that various changes and modifications can be made therein without departing from the spirit and scope thereof.

What is claimed is:

1. A silver halide color photographic light-sensitive material comprising a support having thereon at least one silver halide emulsion layer, the color photographic light-sensitive material having a photographic layer containing at least one kind of magenta coupler represented by the following general formula (I) or (II):

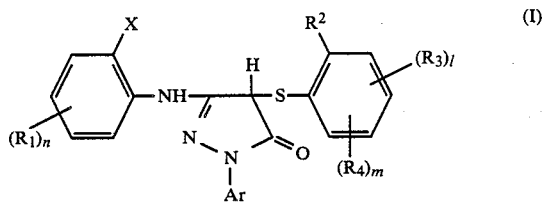

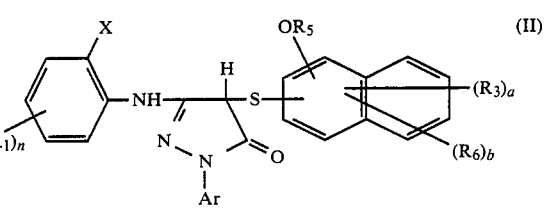

wherein Ar represents a phenyl group substituted with at least one of a halogen atom, an alkyl group, an alkoxy group, an alkoxy group, an alkoxycarbonyl group or a cyano group; X represents a halogen atom or an alkoxy group; $R_1$ represents hydrogen, a halogen atom, an alkyl group, an alkoxy group, an acylamino group, a sulfonamido group, a sulfamoyl group, a carbamoyl group, a diacylamino group, an alkoxycarbonyl group, an alkoxysulfonyl group, an aryloxysulfonyl group, an alkanesulfonyl group, an arylsulfonyl group, an alkylthio group, an arylthio group, an alkyloxycarbonylamino group, a ureido group, an acyl group, a nitro group or a carboxy group; $R_2$ represents a halogen atom, a hydroxy group, an amino group, an alkyl group, an alkoxy group or an aryl group; $R_3$ represents an unsubstituted amino group, an N-alkylamino group, an N,N-dialkylamino group, an N-anilino group, an N-alkyl-N-arylamino group or a heterocyclic amino group, an acylamino group, a ureido group, an alkoxycarbonylamino group, an imido group, a sulfonamido group, a sulfamoylamino group, a nitro group, an alkoxycarbonyl group, a carbamoyl group, an acyl group, a cyano group or an alkylthio group; $R_4$ represents hydrogen, a halogen atom, a hydroxy group, a straight chain or branched chain alkyl group, an aralkyl group, an alkenyl group, a cycloalkyl group or a cycloalkenyl group, an alkoxy group or an unsubstituted or substituted phenyl group having from 6 to 38 carbon atoms or an α- or β-naphthyl group, at least one of $R_2$ and $R_4$ represents an alkoxy group; n represents an integer of from 1 to 4; m is an integer of from 1 to 3; l is an integer of from 1 to 3; $R_5$ represents an alkyl group or an aryl group; $R_6$ represents hydrogen, a halogen atom, an alkyl group, an alkoxy group or an aryl group; a is an integer of from 1 to 5; and b is an integer of from 1 to 5.

2. A silver halide color photographic light-sensitive material as claimed in claim 1, wherein the alkyl moiety included in the alkyl group, the alkoxy group or the alkoxycarbonyl group as the substituent for the phenyl group represented by Ar has from 1 to 22 carbon atoms.

3. A silver halide color photographic light-sensitive material as claimed in claim 1, wherein the alkoxy group represented by X is an alkoxy group having from 1 to 22 carbon atoms.

4. A silver halide color photographic light-sensitive material as claimed in claim 1, wherein the alkyl moiety included in the substituent represented by $R_1$ has from 1 to 36 carbon atoms.

5. A silver halide color photographic light-sensitive material as claimed in claim 1, wherein the aryl moiety included in the substituent represented by the $R_1$ has from 6 to 38 carbon atoms.

6. A silver halide color photographic light-sensitive material as claimed in claim 1, wherein the amino group represented by $R_2$ is an unsubstituted amino group, an N-alkylamino group, an N,N-dialkylamino group, an N-anilino group, an N-alkyl-N-arylamino group or a heterocyclic amino group.

7. A silver halide color photographic light-sensitive material as claimed in claim 1, wherein the alkyl group represented by $R_2$ is a straight chain or branched chain alkyl group, an aralkyl group, an alkenyl group, a cycloalkyl group or a cycloalkenyl group.

8. A silver halide color photographic light-sensitive material as claimed in claim 1, wherein the aryl group represented by $R_2$ is an unsubstituted or substituted phenyl group having from 6 to 38 carbon atoms or an α- or β-naphthyl group.

9. A silver halide color photographic light-sensitive material as claimed in claim 1, wherein the alkyl group represented by $R_5$ is a straight chain or branched chain alkyl group, an aralkyl group, an alkenyl group, a cycloalkyl group or a cycloalkenyl group.

10. A silver halide color photographic light-sensitive material as claimed in claim 1, wherein the aryl group represented by $R_5$ is an unsubstituted or substituted phenyl group having from 6 to 38 carbon atoms or an α- or β-naphthyl group.

11. A silver halide color photographic light-sensitive material as claimed in claim 1, wherein the alkyl group represented by $R_6$ is a straight chain or branched chain alkyl group, an aralkyl group, an alkenyl group, a cycloalkyl group or a cycloalkenyl group.

12. A silver halide color photographic light-sensitive material as claimed in claim 1, wherein the aryl group represented by $R_6$ is an unsubstituted or substituted phenyl group having from 6 to 38 carbon atoms or an α- or β-naphthyl group.

13. A silver halide color photographic light-sensitive material as claimed in claim 1, wherein the magenta coupler represented by the general formula (I) or (II) is a compound represented by the following general formula (III):

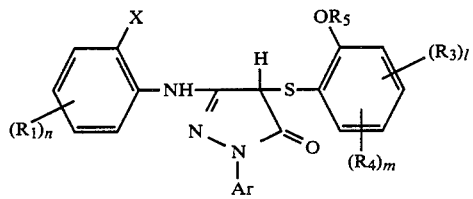

wherein Ar, X, $R_1$, $R_3$, $R_4$, $R_5$, l, m and n each has the same meaning as defined in claim 1.

14. A silver halide color photographic light-sensitive material as claimed in claim 1, wherein the magenta coupler represented by the general formula (I) or (II) is a compound represented by the following general formula (IV):

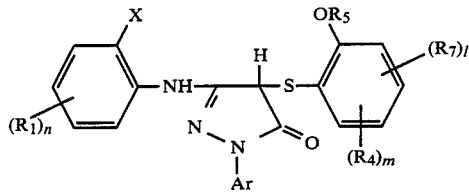

wherein Ar, X, $R_1$, $R_4$, $R_5$, l, m and n each has the same meaning as defined in claim 1, and $R_7$ represents an amino group, an acylamino group, a ureido group, an alkoxycarbonylamino group, an imido group, a sulfonamide group, a sulfamoylamino group or a nitro group.

15. A silver halide color photographic light-sensitive material as claimed in claim 1, wherein the magenta coupler represented by the general formula (I) or (II) is present in a silver halide emulsion layer.

16. A silver halide color photographic light-sensitive material as claimed in claim 15, wherein the magenta coupler is present in an amount ranging from about $2 \times 10^{-3}$ mol to about $5 \times 10^{-1}$ mol per mol of silver in the silver halide emulsion layer.

17. A silver halide color photographic light-sensitive material as claimed in claim 1, wherein the magenta coupler represented by the general formula (I) or (II) is present in a droplet of an organic solvent having a boiling point of not less than about 180° C. dispersed in a hydrophilic colloid.

18. A silver halide color photographic light-sensitive material as claimed in claim 17, wherein the organic solvent is an alkyl ester of phosphoric acid.

19. A silver halide color photographic light-sensitive material as claimed in claim 17, wherein the hydrophilic colloid is gelatin.

20. A silver halide color photographic light-sensitive material as claimed in claim 15, wherein the silver halide emulsion layer is a green-sensitive silver halide emulsion layer.

21. A silver halide color photographic light-sensitive material as claimed in claim 20, wherein the photographic material further comprises a blue-sensitive silver halide emulsion layer containing a yellow color-forming coupler and a red-sensitive silver halide emulsion layer containing a cyan color-forming coupler.

22. A silver halide color photographic light-sensitive material as claimed in claim 21, wherein the photographic material is a color printing paper.

23. A method of forming a color image comprising imagewise exposing a silver halide color photographic light-sensitive material as claimed in claim 1 and developing said material with an aqueous alkaline solution containing a color developing agent.

24. A method of forming a color image as claimed in claim 23, wherein the photographic material is, after color development, processed in a bleach-fixing solution.

25. A method of forming a color image as claimed in claim 24, wherein the color development step and the bleach-fixing step are carried out continuously.

26. A method of forming a color image as claimed in claim 25, wherein the color development solution and the bleach-fixing solution are replenished.

* * * * *